(12) United States Patent
Fusco

(10) Patent No.: US 9,029,312 B2
(45) Date of Patent: May 12, 2015

(54) COMPOSITIONS FOR CLEANING APPLICATORS FOR HAIR REMOVAL COMPOSITIONS

(76) Inventor: Normajean Fusco, Unionville, NY (US)

( * ) Notice: Subject to any disclaimer, the term of this patent is extended or adjusted under 35 U.S.C. 154(b) by 504 days.

(21) Appl. No.: 13/607,698

(22) Filed: Sep. 8, 2012

(65) Prior Publication Data

US 2014/0068874 A1    Mar. 13, 2014

(51) Int. Cl.

| | |
|---|---|
| A61K 9/06 | (2006.01) |
| A61Q 9/04 | (2006.01) |
| C11D 3/18 | (2006.01) |
| C11D 3/48 | (2006.01) |
| C11D 7/24 | (2006.01) |
| C11D 7/50 | (2006.01) |
| C11D 9/24 | (2006.01) |
| A01N 31/16 | (2006.01) |
| A45D 26/00 | (2006.01) |
| A61K 8/31 | (2006.01) |
| A61K 8/34 | (2006.01) |
| A61Q 17/00 | (2006.01) |

(52) U.S. Cl.
CPC *A01N 31/16* (2013.01); *A61Q 9/04* (2013.01); *A45D 26/00* (2013.01); *A45D 26/0019* (2013.01); *A61K 8/31* (2013.01); *A61K 8/34* (2013.01); *A61K 8/347* (2013.01); *A61Q 17/005* (2013.01); *A61K 2800/24* (2013.01); *A61K 2800/87* (2013.01)

(58) Field of Classification Search
CPC ............ A61K 9/06; A61Q 9/04; C11D 3/18; C11D 3/48; C11D 3/485; C11D 7/24; C11D 7/50; C11D 7/5004; C11D 7/5027; C11D 7/5072; C11D 9/24
See application file for complete search history.

(56) References Cited

U.S. PATENT DOCUMENTS

| | | |
|---|---|---|
| D119,329 S | 8/1938 | Leyne |
| D190,067 S | 4/1961 | Reedy |
| D276,192 S | 11/1984 | Fusco |
| D307,331 S | 4/1990 | Pflieger |
| 5,980,536 A | 11/1999 | Jamali |
| 6,204,230 B1 | 3/2001 | Taylor et al. |
| 6,238,682 B1 * | 5/2001 | Klofta et al. .................. 424/402 |
| 6,241,978 B1 | 6/2001 | Schlaeger |
| 6,312,678 B1 | 11/2001 | Elliott |
| 6,599,513 B2 | 7/2003 | Deckers et al. |
| 7,078,050 B2 | 7/2006 | Fusco |
| 7,507,936 B2 | 3/2009 | Mast et al. |
| 7,759,327 B2 | 7/2010 | Modak et al. |
| 8,124,577 B2 | 2/2012 | Bernhardt et al. |
| 8,157,814 B2 | 4/2012 | Kelsey et al. |
| 2001/0028891 A1 * | 10/2001 | Schlaeger ...................... 424/401 |
| 2003/0220416 A1 * | 11/2003 | Montgomery et al. ........ 523/122 |
| 2004/0014818 A1 * | 1/2004 | Boeck et al. ................... 514/731 |
| 2004/0147189 A1 * | 7/2004 | Smith et al. .................... 442/121 |
| 2005/0249758 A1 * | 11/2005 | Di Puccio Pagano ........ 424/401 |
| 2005/0271609 A1 * | 12/2005 | Fei et al. .......................... 424/65 |
| 2007/0122374 A1 * | 5/2007 | Trivedi .......................... 424/76.2 |
| 2008/0107751 A1 * | 5/2008 | Hudnall et al. ............... 424/522 |
| 2009/0017243 A1 * | 1/2009 | Person Hei et al. .......... 428/35.7 |
| 2009/0117067 A1 * | 5/2009 | Baltimore .................... 424/70.6 |
| 2009/0226384 A1 | 9/2009 | Mukhopadhyay et al. |
| 2009/0226541 A1 * | 9/2009 | Scholz et al. ................. 424/672 |
| 2009/0285871 A1 | 11/2009 | Cunningham et al. |
| 2010/0158986 A1 | 6/2010 | Decker et al. |
| 2010/0172847 A1 | 7/2010 | Modak et al. |
| 2010/0196692 A1 * | 8/2010 | Lodha et al. .................. 428/221 |
| 2010/0249227 A1 | 9/2010 | Modak et al. |
| 2012/0027702 A1 * | 2/2012 | Bernoud et al. ................ 424/59 |

* cited by examiner

*Primary Examiner* — Charles Boyer
(74) *Attorney, Agent, or Firm* — Michael E. Zall

(57) ABSTRACT

A non-aqueous liquid cleaning composition for applicators used for applying non-aqueous hair removal compositions to the skin. The composition includes a solubilizing oil effective for solubilizing the non-aqueous hair removal composition, e.g., mineral oil, and an effective antibacterial amount of an antibacterial agent, e.g., triclosan. The composition may also include fragrances and additional bacteriocides, e.g., phenoxyethanol. When the applicator is contacted with the heated cleaning composition any hair removal composition and bacteria on the applicator are removed therefrom and the applicator is ready for reuse. It is preferred to use surgical stainless steel applicators. Also provided are methods of using these compositions and kits containing, among other items, such compositions and applicators.

15 Claims, 8 Drawing Sheets

FIG. 9
FIG. 10
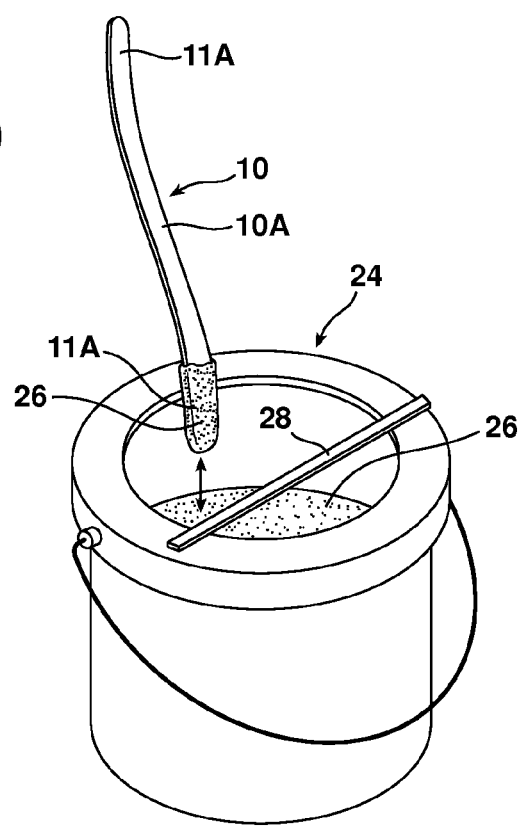
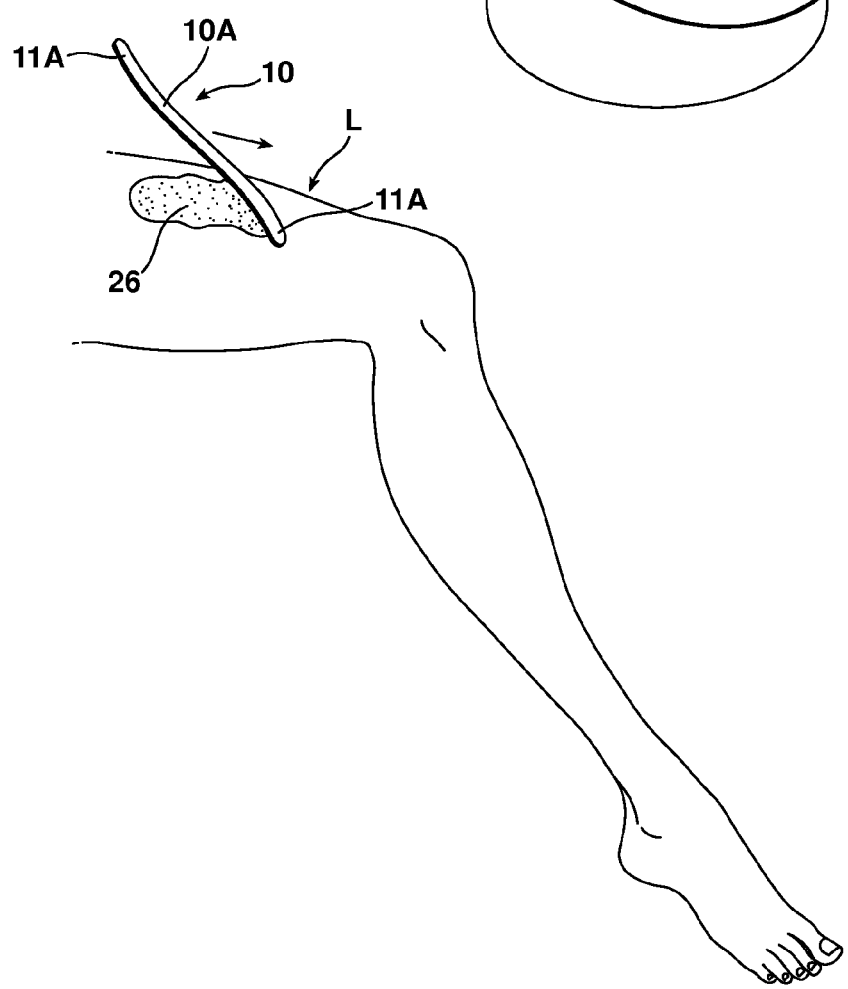

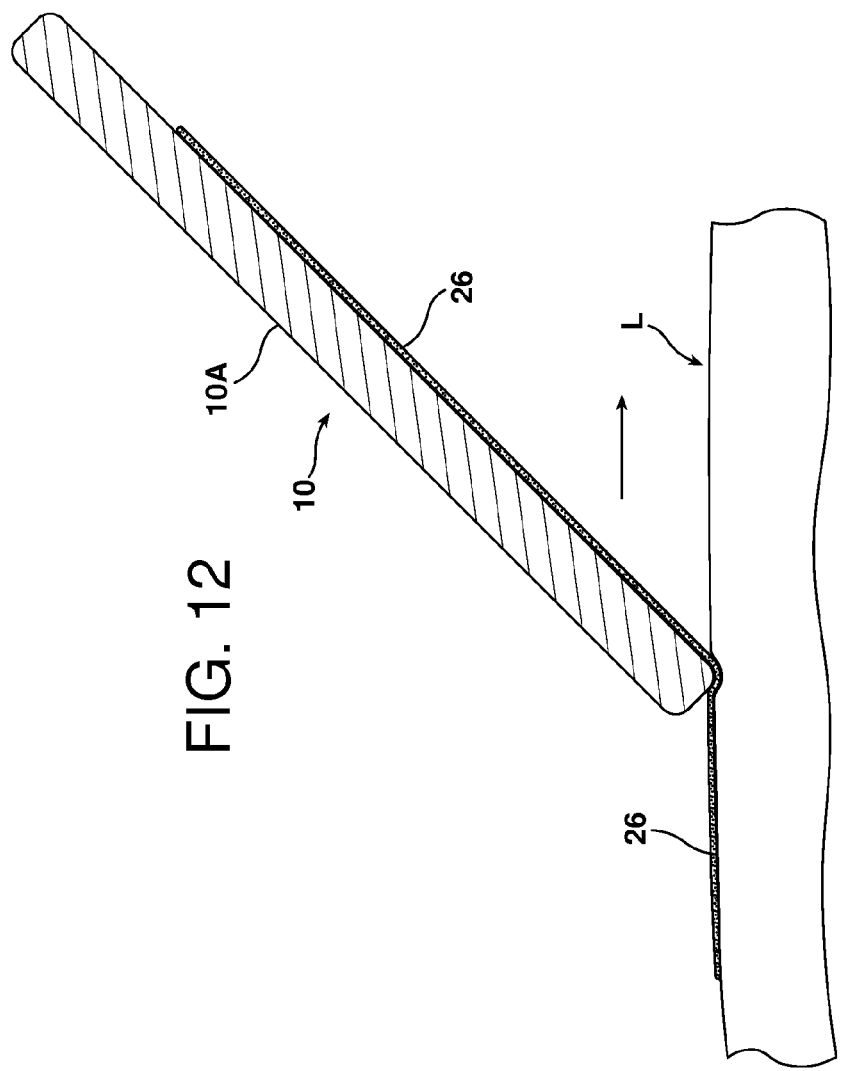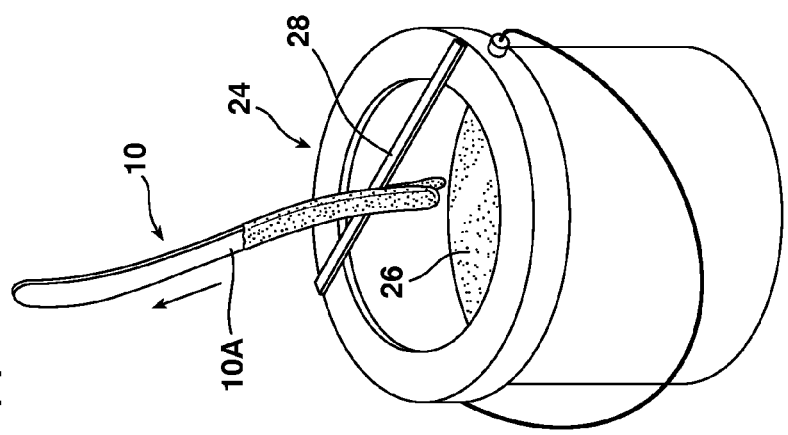

COMPOSITIONS FOR CLEANING APPLICATORS FOR HAIR REMOVAL COMPOSITIONS

BACKGROUND OF THE INVENTION

1. Field of the Invention

The present invention relates to non-aqueous, i.e., anhydrous, cleaning compositions for applicators used for applying non-aqueous, i.e., anhydrous hair removal compositions to the skin. The cleaning composition comprises a solubilizing oil effective for solubilizing the non-aqueous hair removal composition, e.g., mineral oil, and an effective amount of an antibacterial agent, e.g., triclosan. The present invention also relates to methods of cleaning such applicators, methods of removing hair and applicator kits using such cleaning compositions.

2. Description of the Related Art

A variety of methods have been developed for removing unwanted hair from various parts of the body. One typical hair removal method is "waxing", a process by which a wax is used to pull unwanted hair out by the root bulb. Warm wax in liquid form is applied to the desired area of the body, and is allowed to cool and harden on the hair to be removed. Typically, in the application of wax to the skin to be treated, use is made of an applicator in the form of a stick. The applicator can be inserted into a bath of hot wax in a wax heater, withdrawn from the bath with adherent molten wax and applied to the skin. Applicators of various widths and shapes may be used in the application process. The wax is then peeled off of the body, removing the unwanted hair with it. Waxing is generally painful and uncomfortable for the person undergoing the wax treatment. In an attempt to eliminate this undesirable aspect of waxing, some technicians place a layer of material, such as a cloth on top of the cooling wax. As the wax cools it adheres to the cloth, so that the technician can pull the cloth to remove the wax. This is still painful and uncomfortable.

Other systems have been used to remove body hair. Depilatory creamshaves been developed that are applied to the skin. The cream will generally degrade the hair to the extent that some hairs are broken, and the remainder weakened. The depilatory cream preparation and hair may be removed from the skin without any mechanical assistance, for example by showering. This method is kind to the skin but tends to be imperfect with respect to efficiency of hair removal. An alternative method is to remove the preparation and hair by means of a spatula, used in the manner of a scraper, removing the cream from the skin, along with broken hairs, and at the same time breaking off weakened hairs, and removing those. This tends to be more effective, but the scraping action can lead to skin coarsening and roughness.

There has also been developed wax free, non-aqueous (anhydrous) liquid depilatories that may be used. These "natural" depilatories are antibacterial, antimicrobial, anhydrous botanical formulas that consist of botanical oils and rosins. The products never dry and do not stick to the skin and are designed to gently remove the hair under lower temperatures than are required for wax and wax-like products that utilize constant heating above 160° F. Such products are sold under the NUFREE® brand (Equibal Labs, Unionville, N.Y.). See also U.S. Pat. No. 7,078,050 to Fusco and the FINIPIL® brand products from Equibal Labs.

The applicators used for such treatments are usually wooden applicators and may be thin stick shape applicators used for eyebrows or flat, spatula type applicators used for the skin surface on the legs, arms, etc. The applicators are made of wood and disposable. Ninety Percent (90%) of the applicators used in salons are wood. About five applicators per service are used, amounting to thousands used over the course of a year. Generally, wood applicators do not get cleaned, plastic applicators usually cannot be effectively cleaned and glass applicators are hazardous. Presently about 10% of the industry uses stainless steel. Very few salons or technicians use medical grade (surgical) stainless steel. The various State cosmetology boards demand that applicators that cannot be efficiently cleaned and sanitized before the next use must be disposed of. Thus, most applicators are disposed of because it is difficult to clean accumulated depilatory and bacteria from such applicators. Thus, the applicators are used only once and discarded.

If reusable applicators are used, such applicators can only be cleaned by using heated, harsh chemicals that must be used in a well ventilated facility. Additionally, even if the facility is well ventilated, such harsh chemical cleaners and conditions are dangerous to customers and spa technicians. Thus, the disposable wooden applicator, which is used once and then disposed of, has become the norm in the industry. Such disposable applicators, although individually inexpensive, can become an expensive part of the costs for running a salon when thousands are used per year. Such applicators can also be considered environmentally undesirable.

When reusable stainless steel applicators are used, the solvents for removing the "waxes" and resin based non-aqueous or anhydrous hair removal compositions require highly flammable and odoriferous solvents to clean them. Such cleaning if used, is usually followed by autoclaving and/or use of alcohol based cleaner. If the applicators are not completely free of the hair removal product the alcohol hardens the residue and the applicator cannot be reused. This is expensive and requires the salon to have many expensive metal applicators.

The present invention addresses the aforementioned deficiencies of wooden applicators and the problems associated with attempts to effectively clean reusable applicators.

The following is a list of US Published applications and US patents related to this art:

U.S. Pat. No. 5,980,536 to Jamali describes a rigid, microwavable container and applicator kit for body wax that includes several microwavable applicators for smoothing the wax onto the skin.

U.S. Pat. No. 6,204,230 to Taylor et al. describes aqueous antibacterial compositions, in particular personal care compositions, that contain a polyhydric solvent, a hydrotrope, a surfactant, an optional antibacterial agent, e.g., triclosan, and water. The compositions provide a substantial reduction, e.g., greater than 99%, in Gram positive and Gram negative bacterial populations within one minute.

U.S. Pat. No. 6,241,978 to Schlaeger describes a cosmetic composition that includes hydrophobic lipophilic materials as the principle vehicle carrying the active ingredients in a continuous solid phase. The composition is formed into a hairstick that is a hair fixative and may include, inter alia, mineral oil, triclosan and fragrance.

U.S. Pat. No. 6,312,678 to Elliott et al. discloses an aqueous rinse-off liquid personal cleansing composition that includes about 1% to about 60% by weight of a water-soluble surfactant, and 0.5% or greater of a water-soluble oil selected. Among the numerous ingredients listed, the compositions can have mineral oil, 2-phenoxyethanol as a preservative and triclosan as an antibacterial agent.

U.S. Pat. No. 6,599,513 to Deckers et al. describes emulsion formulations for topical application which include oil bodies and other ingredients, e.g., triclosan as antimicrobial, and Neolone as a preservative agent.

U.S. Pat. No. 7,078,050 to Fusco discloses a white cream bacteriostat and fungicide capable of serving as a vehicle for additional medicaments. Also disclosed is a method for blending the ingredients, some of which are not readily compatible with each other.

U.S. Pat. No. 7,507,936 to Mast et al. describes a wax applicator stick scraper for scraping wax, and especially excess wax from a stick used in applying wax to the skin for wax treatment and/or depilation.

U.S. Pat. No. 7,759,327 and US 2010/0249227 to Modak et al. discloses methods and compositions which employ low concentrations of combinations of zinc salts and antimicrobial agents in coatings for medical articles that contact the skin, including depilatories, waxing and razors. The coatings have an anti-irritant effect and inhibit transmission of infectious disease. More specifically, the compositions include water soluble zinc salts, an emollient form based on petrolatum or mineral oil, phenoxyethanol, fragrances, and triclosan and/or phenoxyethanol as antimicrobial or preservative agents.

U.S. Pat. No. 8,124,577 to Bernhardt et al. describes formulations of personal care compositions and personal care concentrate compositions, e.g., liquid hand soaps, bath and shower washes, shampoos, 2-in-1 or 3-in-1 shampoos, anti-dandruff shampoo, facial cleaners, that contain sulfo-estolides. Such compositions may also include mineral oil, Neolone, triclosan and fragrances.

U.S. Pat. No. 8,157,814 to Kelsey et al. discloses an S-section plastic spatula design for depilatory application.

US 2005/0152861 to Bruening et al. discloses a water-in-oil emulsion antiperspirant compositions containing: (a) an antiperspirant component; (b) a polyol-poly-12-hydroxystearate; (c) an oil component; and (d) water. The antiperspirant may also contains phenoxyethanol and Irgasan® (triclosan).

US 2008/0004635 to McMillan et al. describes a spatula for aiding in the removal of a hardened wax from a person's body.

US 2009/0226384 to Mukhopadhyay et al. discloses an antimicrobial composition containing triclosan and at least one functionalized hydrocarbon and/or mixtures containing such functionalized hydrocarbons. The ratio of triclosan to that of the functionalized hydrocarbon and/or mixtures containing such functionalized hydrocarbons may be in the range of 1:5-1:100. The composition is useful as an antimicrobial composition which includes hair care, skin care, oral care, surface cleaning and similar compositions used to cleanse and/or treat any living or non-living surface.

US 2009/0285871 to Cunningham et al. discloses a germicidal wipe having a germicidal solution of at least one peracid, at least one peroxide, and a surfactant. The solution may also have Neolone and Symocide PT.

US 2010/0158986 to Decker et al. describes personal care compositions and personal care products that impart perceivable aesthetic benefits of increased softness, quietness and drapability to the skin or hair of a user. The compositions may include a mineral oil, fragrances, and Symocide PT.

US 2010/0172847 to Modak et al. discloses preservative or antimicrobial compositions with broad spectrum antimicrobial activity comprising low concentrations of essential oil (and/or one or more components thereof) and a botanical extract in synergistic combination with a fruit acid and alkanediol, and optionally a solvent. The compositions of the invention may be used in personal care products such as creams or soap products. An antibacterial composition is disclosed that includes botanical extracts and solvents such as vegetable oils, phenoxyethanol as non-alkanediol alcohol at 0.5-4%, and Triclosan for application to varying surfaces. The composition is capable of killing *S. aureus*.

Design patents showing cosmetic applicators:
U.S. D307331 to Pflieger.
U.S. D190067 to Reedy.
U.S. D119329 to Leyne.

OBJECTS AND SUMMARY OF INVENTION

It is an object of this invention to provide compositions, procedures and kits that allow applicators used for applying non-aqueous, i.e., anhydrous, hair removal compositions to be safely cleaned and sterilized for reuse.

It is yet another object of this invention to replace the ubiquitous disposable wooden applicators with surgical stainless steel applicators that can be safely and economically cleaned and sterilized for reuse with aqueous, i.e., anhydrous, hair removal compositions.

It is still another object of this invention is to provide an efficacious non-aqueous liquid cleaning composition for such applicators that can be used at relatively safe temperatures and does not emit toxic or noxious fumes.

It is yet another object of this invention provide a non-aqueous liquid cleaning composition that is effective and safe for cleaning and sterilizing such applicators and that is effective at relatively low temperatures, e.g., less than 135° F., preferably exceeding 125° F.

All of the foregoing objects as well as others are achieved by the use of a non-aqueous liquid cleaning composition for applicators used for applying non-aqueous hair removal compositions to the skin. The composition includes a solubilizing oil, e.g., mineral oil, that is effective for solubilizing the non-aqueous hair removal composition, and an effective antibacterial amount of an antibacterial agent, e.g., triclosan. The composition may also include fragrances and additional bacteriocides, e.g., phenoxyethanol. When the applicator is contacted with the cleaning composition any hair removal composition and bacteria on the applicator are removed therefrom and the applicator is ready for reuse. It is preferred to use surgical stainless steel applicators.

A specifically preferred composition includes:
97.7% by weight by weight of white mineral oil,
0.3% by weight by weight of triclosan as antibacterial agent,
1.0% by weight Neolone PH 100 (phenoxyethanol active) as an additional antibacterial ingredient, and
1.0% by weight Symocide PS as a fragrance. Symocide PS is a mixture of phenoxyethanol, 1,2-hexandiol, and decylene glycol.

The invention is also directed to methods and kits for cleaning a contaminated applicator used for applying a non-aqueous hair removal composition to a person's skin. The method includes:

a. Providing a liquid non-aqueous cleaning composition comprising a solubilizing oil effective for solubilizing the non-aqueous hair removal composition, e.g., mineral oil, and an effective antibacterial amount of an antibacterial agent, e.g., triclosan;

b. Providing a heater cup;

c. Filling the heater cup with an amount of the cleaning composition;

d. Heating the cleaning composition contained in the cup to a temperature sufficient to solubilize the non-aqueous hair removal composition e.g., a temperature between about 115° F. to about 135° F., to produce a heated cleaning composition;

e. Providing a contaminated applicator having thereon a residual amount of the hair removal composition and bacteria;

f. Contacting the contaminated applicator with the heated cleaning composition for a period of time to remove the residual amount of hair removal composition thereon and substantially all the bacteria thereon; and then g. Wiping the applicator with a fabric material to remove any cleaning composition remaining on the applicator;

h. Applying to a person's skin with the applicator the hair removal composition to produce the contaminated applicator;

i. Repeating steps f through i.

Applicant describes herein numerous embodiments of the invention in conjunction with the drawings, which include variations in the different elements of the invention.

BRIEF DESCRIPTION OF THE DRAWINGS

The novel features believed to be characteristic of the present invention, together with further advantages thereof, will be better understood from the following description considered in connection with the accompanying drawings in which several embodiments of the invention are illustrated by way of example. It is to be expressly understood, however, that the drawings are for the purpose of illustration and description only and are not intended as a definition of the limits of the invention.

FIG. 9 depicts contacting a spatula type applicator with the hair removal composition to provide an applicator having the hair removal composition thereon.

FIG. 10 depicts applying the hair removal composition to a person's leg with the applicator.

FIG. 11 depicts a technique for contacting an applicator with the hair removal composition.

FIG. 12 depicts a detailed cross-sectional view applying the hair removal composition to a person's skin with the applicator.

DETAILED DESCRIPTION OF THE INVENTION

Figure 1:
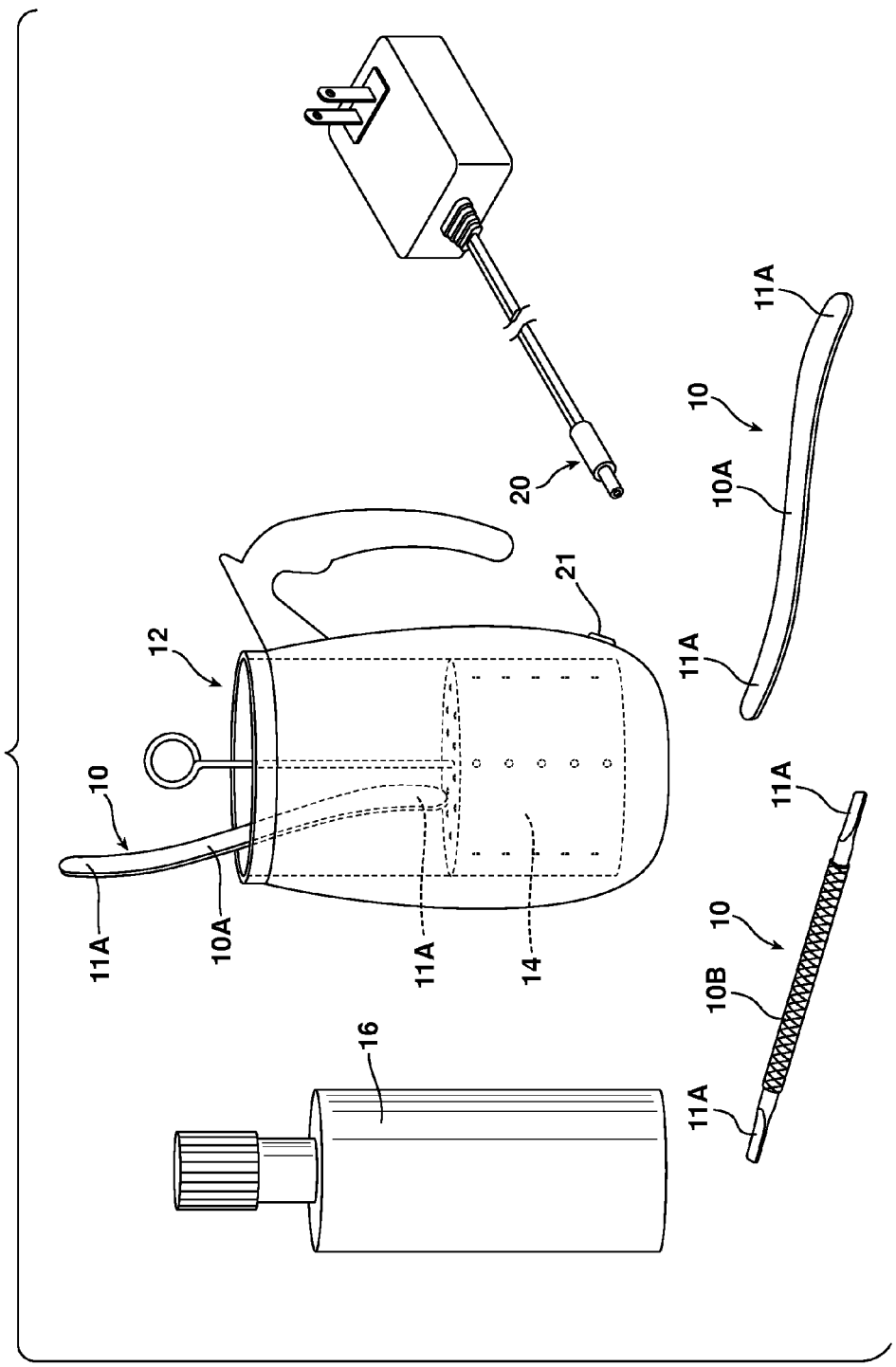
FIG. 1 shows the component elements used in the method and kit for cleaning contaminated applicators used for applying non-aqueous hair removal compositions.
Figure 2:
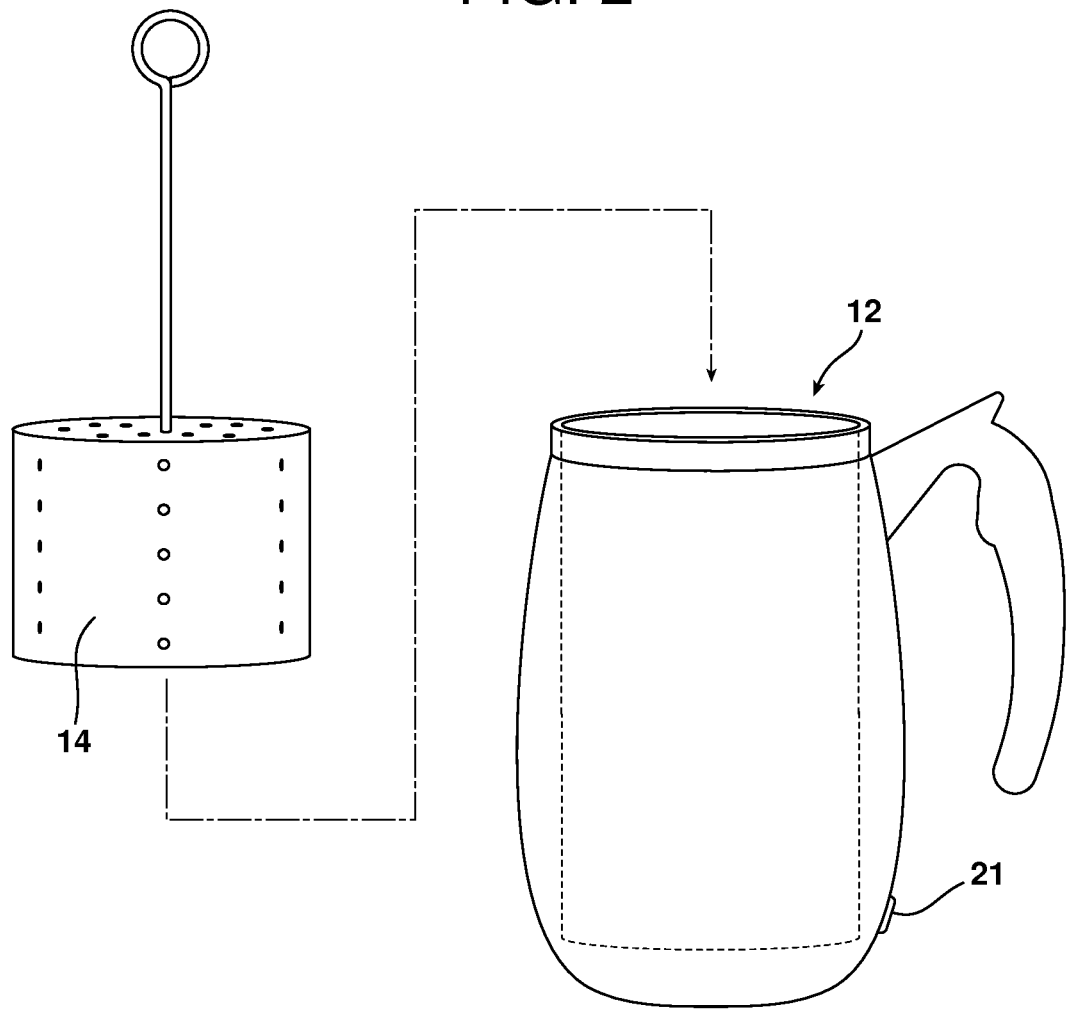
FIG. 2 shows an example of an electric heater cup and basket for the cleaning compositions of this invention used in the methods and kits of this invention.
Figure 3:
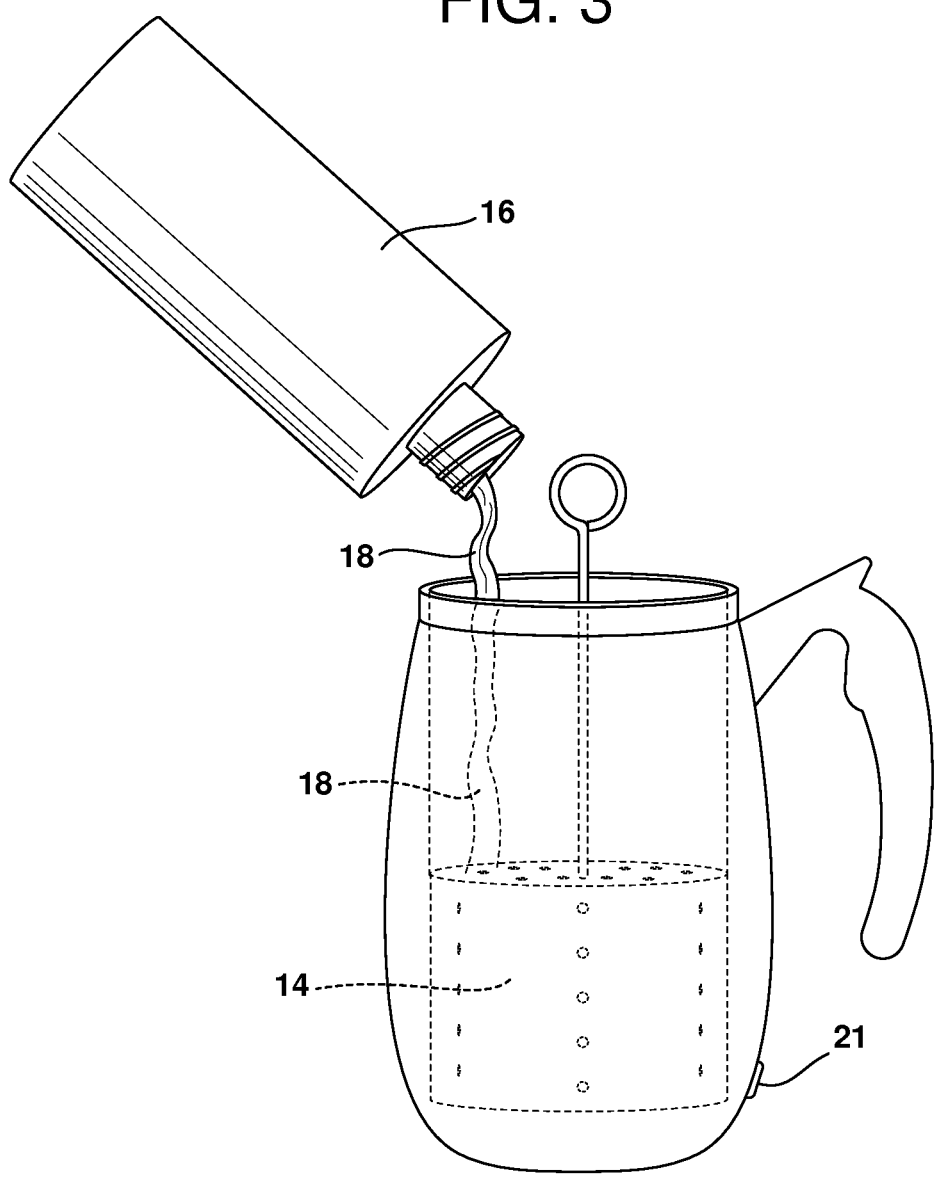
FIG. 3 depicts filling the heater cup with an amount of the cleaning composition of this invention.
Figure 4:
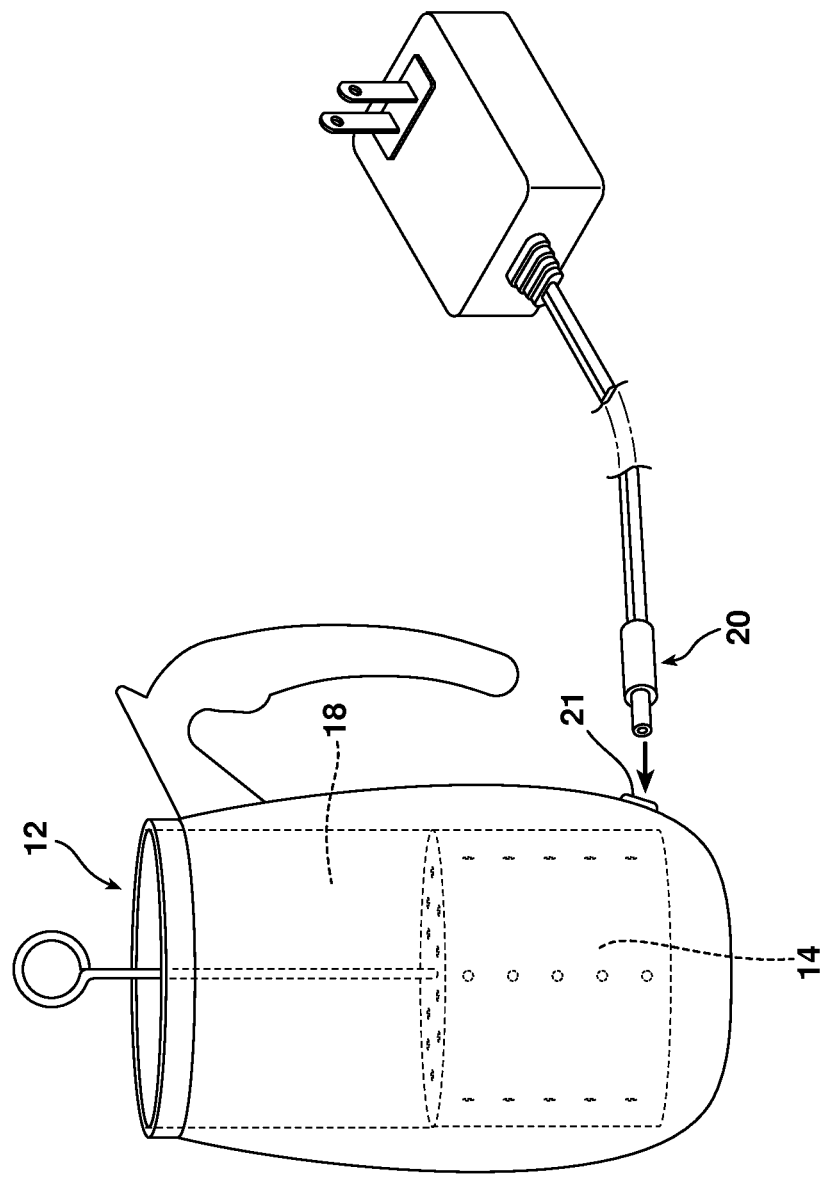
FIG. 4 depicts the heater cup with an amount of the cleaning composition therein just prior to connecting the electric power thereto for heating the composition.

This invention is directed to non-aqueous liquid cleaning composition for applicators used for applying non-aqueous hair removal compositions to the skin.

The applicators used in this invention are preferably medical grade stainless steel applicators depicted in the Figures as 10. Although such material of construction for such applicators is preferred, this invention contemplates any type material, e.g., polymeric or metallic, that can be effectively used to apply the hair removal composition and can be cleaned as described herein to provide an applicator that is commercially and legally acceptable, e.g., substantially free of bacteria and hair removal composition. In the Figures two types of applicators are depicted, i.e., a body applicator 10A and an eyebrow applicator 10B.

The preferred applicators 10 used in this invention are Japanese medical grade stainless steel that can be efficiently cleaned by the compositions and methods of this invention. Lower quality stainless steel is not desirable, although can be used, because it may pit and scratch and therefore presents a problem for proper and thorough cleaning. However the cleaning compositions and methods will work with any high grade stainless steel applicator.

The hair removal composition is a non-aqueous "anhydrous" hair removal composition, preferably a wax free, non-aqueous (anhydrous) liquid depilatory that is a "natural" depilatory. Such depilatory is typically an antibacterial, antimicrobial, anhydrous botanical formulation that consists of botanical oils and rosins. The products do not dry and stick to the skin and are designed to gently remove the hair under lower temperatures than are required for wax and wax-like products that utilize constant heating above 160° F. Such products, for example, are sold under the NUFREE® brand (Equibal Labs, Unionville, N.Y.).

The cleaning composition comprises a solubilizing oil effective for solubilizing the non-aqueous hair removal composition. The preferred oil for use in the cleaning composition of this invention is mineral oil, i.e., an insoluble cosmetic oil which also acts as emollient for the ingredients and the non-aqueous (anhydrous) hair removal composition. It is a hydrophobic or water repellent substance. It is also non-toxic, colorless, transparent, odorless and tasteless, and, when heated, smells like petroleum.

Although mineral oils are preferred, other hydrocarbon oils may be used such as rapeseed oil, theobroma oil, castor oil, jojoba oil, silicone oil, lanolin, olive oil, cocoa butter, and shea butter and various fragrances and essential oils selected to solubilize the specific non-aqueous hair removal composition at relatively low temperatures, i.e., commercially safe temperatures, and capable of holding therein an effective amount of the selected antibacterial agent or agents.

Additional solubilizing oils that may be included in the cleaning composition of this invention are hydrocarbon-based emollients such as petrolatum, fatty ester-based emollients, such as methyl, isopropyl and butyl esters of fatty acids such as isopropyl palmitate, isopropyl myristate, isopropyl isostearate, isostearyl isostearate, diisopropylsebacate, and propylene dipelargonate, 2-ethylhexyl isononoate, 2-ethylhexyl stearate, C(12)-C(16) fatty alcohol lactates such as cetyl lactate and lauryl lactate, isopropyl lanolate, 2-ethylhexyl salicylate, cetylmyristate, oleylmyristate, oleyl stearate, oleyloleate, hexyl laurate, and isohexyllaurate.

In the preferred cleaning composition of this invention the solubilizing oil is mineral oil that is present at from about 96.5% to about 98.9% weight percent of the cleaning composition.

The cleaning composition further includes an effective antibacterial amount of an antibacterial agent. The preferred agent is triclosan (TCS), a chlorinateddiphenyl ether, an antimicrobial agent that has been employed for a variety of purposes for more than 20 years. Triclosan is preferred based on its efficacy and its solubility in the selected solubilizing oil.

Triclosan has an exceedingly low solubility in water, e.g., 5 to 10 ppm and a relatively high solubility in mineral oil.

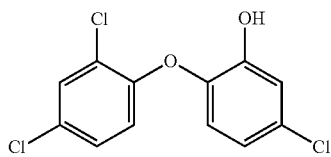

Chemical Name:
2,4,4'Trichlorl-2'-Hydroxydiphenyl Ether
Phenol 5-chloro-2-(2,4-clichlorophenoxy)
CAS Number 3380-34-5

Triclosan is relatively non-toxic to humans and other mammals. It is also not found to have any carcinogenic, mutagenic or teratogenic effects. (Bhargava H N & Leonard P A: Triclosan—Applications and Safety. Am. Jour. Infect. Cont., (1996), 24 (3): 209-218). It is used clinically, in oral hygiene products as well as in a wide range of consumer products. Triclosan has a broad range of activity that encompasses many, but not all types of Gram positive and Gram negative non-sporulating bacteria, some fungi and viruses. Triclosan is marketed by Ciba-Geigy of Basle, Switzerland, under the name of Irgasan.

The cleaning compositions of the invention may alternatively or optionally include one or more additional antibacterial or anti-microbial agents that can be carried in, e.g., solubilized or emulsified, in the selected solubilizing oil. The agent should have a low water content and/or not need water so that it can blend with the selected solubilizing oil needed to remove the non-aqueous hair removal composition.

Examples of agents that may be used include, but are not limited to, chitosan, phenoxyethanol, chlorhexidinegluconate, iodophores, iodine, benzoic acid, dehydroacetic acid, propionic acid, sorbic acid, methyl paraben, ethyl paraben, propyl paraben, butyl paraben, isobutyl paraben, cetrimide, chlorhexidine (free base and/or salts), other biguanides, chloroerosol, chloroxylenol, benzyl alcohol, bronopol, benzalkonium chloride, benzethonium chloride, ethanol, phenoxyethanol, phenyl ethyl alcohol, 2,4-dichlorobenzyl alcohol, thiomersal, clindamycin, erythromycin, benzoyl peroxide, mupirocin, bacitracin, polymixin B, DMDM Hydantoin (Glydant), GERMALL, Kathon CG, Phenonip, miconazole, fluconazole, itraconazole, etcn-alkyl dimethyl benzyl ammonium chloride, n-alkyl dimethyl benzyl ammonium chloride, dialkyl dimethyl ammonium chloride, didecyl dimethyl ammonium chloride, dioctyl dimethyl ammonium chloride, phenolics, iodophors, pine oil, methyl salicylate, morpholine, silver, copper, bromine, and quaternary ammonium compounds, derivatives thereof, and combinations thereof. Antibacterial perfumes such as, for example, thymol, thyme oil, eugenol, clove oil, menthol, mint oil, farnesol, and antibacterial glycerol esters such as, for example, glycerol monocaprate, glycerol monocaprylate, glycerol monolaurate (GML) and diglycerolmonocaprate (DMC) may also be used.

The most common forms of bacteria and fungus which are the cause of most irritations or infections are *Staphylococcus aureus* (ATCC 6538); *Pseudomonas aeruginosa* (ATCC 9027); and *E. coli* (ATCC 8739). Common forms of fungi include *Aspergillus niger* (ATCC 16404); and *Candida albicans* (ATCC 10231).

The preferred cleaning composition of this invention includes one or more antimicrobial agents, preferably at a total concentration between 0.01 and 5 weight percent or between 0.05 and 3% by weight or between 0.1% and 2% by weight. In the preferred cleaning composition using the preferred mineral oil there is from about 0.1% to about 0.5%, preferably 0.3% by weight of triclosan and about 0.5% to about 1.5% by weight of phenoxyethanol.

Additional ingredients may be added to the cleaning composition of this invention, for example fragrances. Fragrances that may be used in accordance with the present invention include any synthetic as well as natural fragrance and mixtures thereof. A multiplicity of fragrances may be used to achieve the desired effect. Apart from their effects as fragrances, such compounds also may be useful in the instant invention as antimicrobial agents and/or preservatives.

Typically a fragrance comprises between about 0.1% by weight to about 5% by weight of the final composition. Generally the amount of such fragrance is not critical.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranellal; phenyl ethyl acetate; phenylethylisobutarate; gamma methyl ionone; geraniol; anethole; benzaldehyde; benzyl acetate; benzyl salicate; linalool; cinnamic alcohol; phenyl acetaldehyde; amyl cinnamic aldehyde; caphore; p-tertiary butyl cyclohexyl acetate; citral; cinnamyl acetate; citral diethyl acetal; coumarin; ethylene brasslate; eugenol; l-menthol; vanillin; and mixtures thereof.

Examples of natural fragrances that may be used herein include, without limitation, lavandin; heliotropin; sandlewood oil; oak moss; pathouly; ambergris tincture; ambrette seed absolute; angelic root oil; bergamont oil; benzoin; Siam resin; buchu leaf oil; cassia oil; cedarwood oil; cassia oil; castoreum; civet absolute; chamomile oil; geranium oil; lemon oil; lavender oil; Ylang Ylang oil; and mixtures thereof.

The preferred fragrance is 1.0% by weight Symocide PS ((Phenoxy Ethanol, 1,2Hexanediol, Decylene Glycol).

The cleaning compositions of this invention may also contain a preservative or preservative system to inhibit the growth of pathogens over an extended period of time. Suitable preservatives for use in the germicidal solution may include, for instance, Kathon CG, which is a mixture of methylchloroisothiazolinone and methylisothiazolinone available from Rohm & Haas; Neolone 950, which is methylisothiazolinone available from Rohm & Haas, Mackstat H 66 (available from McIntyre Group, Chicago, Ill.); DMDM hydantoin (e.g., Glydant Plus, Lonza, Inc., Fair Lawn, N.J.); iodopropynylbutylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1, 3-diol; benzoic acid; imidazolidinyl urea; diazolidinyl urea; and the like. Still other preservatives may include ethylhexylglycerin (Sensiva SC 50 by Schulke&Mayr), phenoxyethanol (Phenoxyethanol by Tri-K Industries), caprylyl glycol (Lexgard O by Inolex Chemical Company, Symdiol 68T (a blend of 1,2-hexanediol, caprylyl glycol and tropolone by Symrise) and Symocide PT (a blend of phenoxyethanol and tropolone by Symrise).

Figure 5:
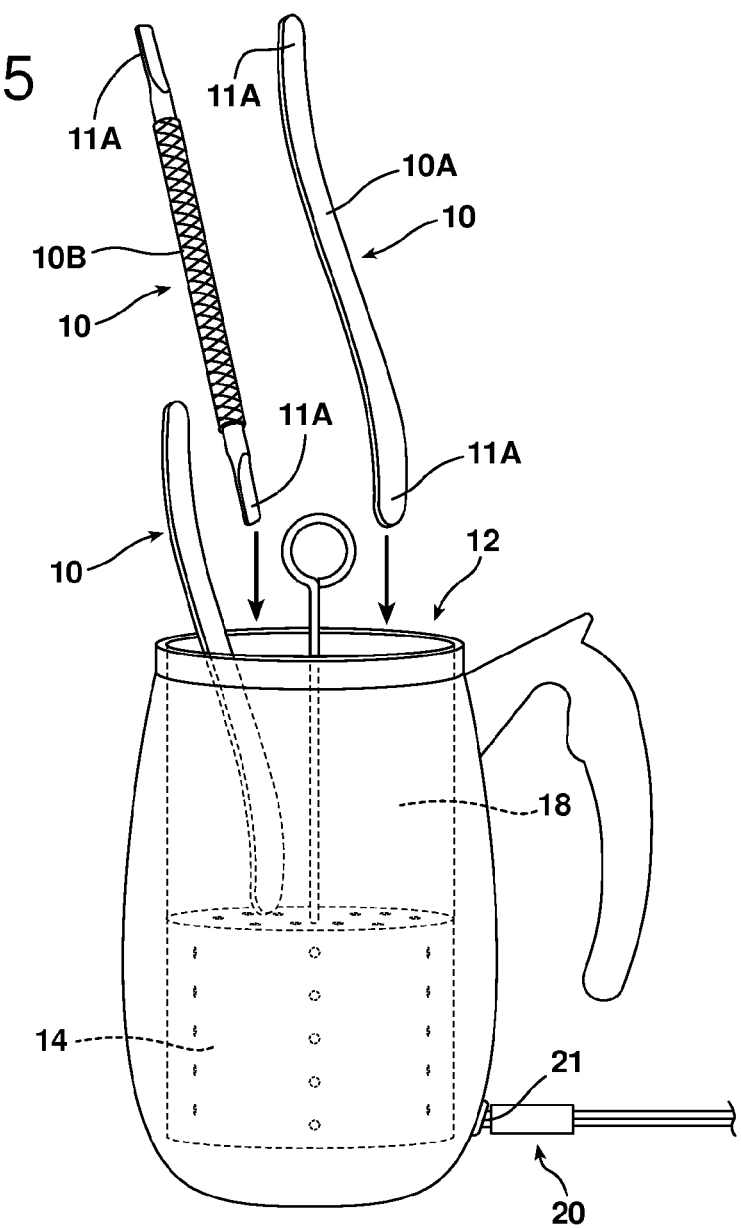
FIG. 5 depicts contacting the contaminated applicator with the heated cleaning composition for a period of time to remove the residual amount of hair removal composition thereon and substantially all the bacteria thereon.

Referring to the Figures, for example FIGS. 1 and 5, when the applicator 10 is contacted with the cleaning composition 18 any hair removal composition and bacteria on the applicator 10 are removed therefrom. The process includes providing a heated non-aqueous hair removal composition 26 and the liquid non-aqueous cleaning composition 18. The cleaning composition 18 is designed primarily for cleaning applicators that use non-aqueous hair removal products, e.g., products sold under the NUFREE® brand (Equibal Labs, Unionville, N.Y.), although this invention contemplates the use of other type non-aqueous hair removal products.

An electric heater cup 14, 20 is provided for the cleaning composition 18. Prior to filling the heater cup 12, the electric plug 20 should not be plugged into the cup 14 and a stainless steel basket 14 that is provided should be completely in the cup 12.

Once the basket 14 is securely in the unit the technician pours the entire contents 18 of one bottle 16 of the cleaning composition (about 0.5 liters). This is the exact amount you need to fill the cup 12. Once the cup 12 is filled, the electric plug 20 is inserted into the base of the cup 12. The unit 12 is designed to stay warm all day long. Never plug in the unit if it is empty. Never leave it plugged in overnight. The cleaning composition 18 contained in the cup 14 is heated to a temperature sufficient to solubilize the non-aqueous hair removal composition 18.

Applicators 10 are provided for applying the hair removal composition 18 to the skin, e.g., the leg L or eyebrow EB. Preferably the applicators 10 are made of medical grade stainless steel.

The use of a stainless steel applicator 10 also permits a finer coating on the applicator 10 thus using less hair removal product 26.

Figure 7:
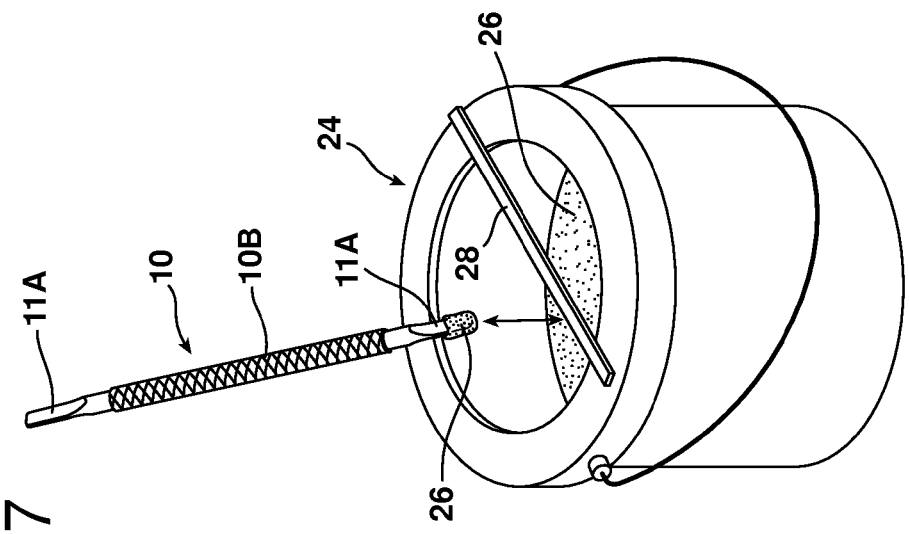
FIG. 7 depicts contacting an eyebrow applicator with the hair removal composition to provide an applicator having the hair removal composition thereon.

Initially a cleaned applicator 10 is contacted with the hair removal composition 26 to provide an applicator 10 having the hair removal composition on the tips 11A of the applicators 10 (see FIGS. 7, 9 and 11). The applicator 10 is then used for applying the hair removal composition 26 to a person's skin.

Referring to FIGS. 7, 9 and 11, the cleaned applicator 10 is then dipped in a hair removal composition 26 held in heated container 24 and the excess is removed by passing the applicator 10 over the scraper bar 28 over the opening of container 24. In FIGS. 7, 9 and 11, a heater 24 is shown into which a hair removal product 26 is placed, e.g., a can containing the product, so that it can be heated. The excess hair removal product can be scraped from the applicator 10 by a scraper bar 28 which can be fitted over an arc of the peripheral edge of the can or heater.

Figure 8:
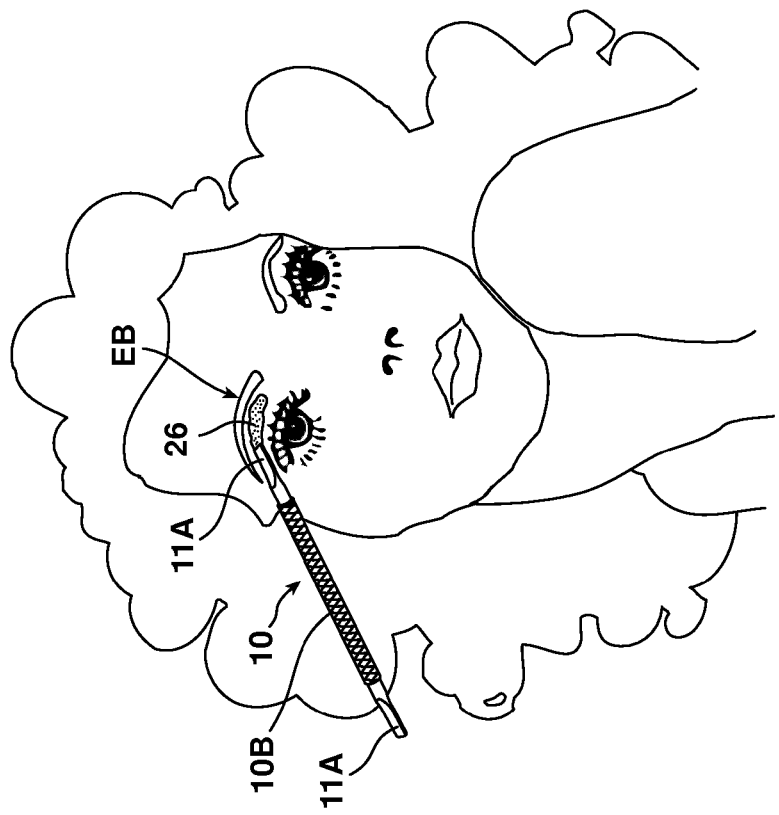
FIG. 8 depicts applying the hair removal composition to a person's eyebrows with the applicator.

In FIGS. 7 and 8, the eyebrow applicator 10B tip 11A is used to apply the hair removal composition 26 to the eyebrow EB for subsequent removal from the eyebrow EB (not shown). In FIGS. 9-12, the body applicator 10A, which has a curved surface on both ends 11A, is used to apply the hair removal composition 26, for example, to the leg L for subsequent removal from the eyebrow leg L (not shown) of the hair removal composition 26 and the hair.

More specifically, referring to FIGS. 7 and 8, when the technician is ready to use the eyebrow applicator 10B he/she will take it out of the cleaning composition 18 held in the cup 12 and dry it thoroughly in a paper towel 22. The applicator tip 11A is then "tapped" into the hair removal composition 26 in heater unit 24 until a little round ball of product is formed on the tip 11A. The tip is then contacted with the scrapper bar 28 to produce a small "ball of product" of sufficient amount to do the whole eyebrow EB. The technician then applies a nice smooth path of product on the hair that needs to be removed. The medical stainless steel applicator 10 applies a thin, even coating of hair removal product 26 on the skin with no harm to the skin.

Again, more specifically, referring to FIGS. 9-12, when the technician is ready to use the body applicator 10A he/she will take it out of the cleaning composition 18, dry it thoroughly with a paper towel or strip 22 so that there is no cleaner on the applicator 10A and then dip the applicator into the heated hair removal composition 26. The tip 11A of the applicator 10A is then scrapped across the scraper bar 28 on one side of the applicator tip 11A (FIG. 11) to clean that side of the applicator tip 11A. The technician then applies the other side of the tip 11A having the hair removal product thereon to the skin, e.g., leg L, at between a 45° angle and 90° to the skin L applying the product in a thin layer onto the skin L. The medical stainless steel applicator 10A enables less product to be used and permits more passes over the skin from one dip than other type applicators.

After application of the hair removal composition 26 to the body, the applicator 10 is contaminated with a residual amount of the hair removal composition 26 and bacteria, primarily but not solely on the tip 11A. Referring to FIG. 5, the contaminated applicator 10 is then contacted with the heated cleaning composition 18 for a period of time to remove the residual amount of hair removal composition thereon and substantially all the bacteria thereon. Generally, the applicator 10 will be sanitized within about 15 seconds and emerge warm and clean.

Figure 6:
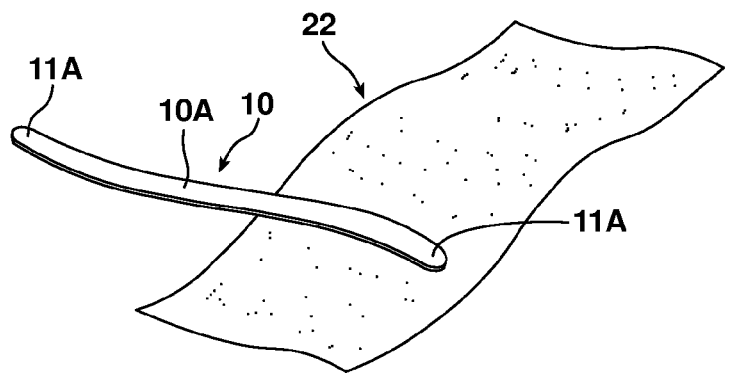
FIG. 6 depicts wiping the applicator with a fabric material to remove any cleaning composition remaining on the applicator prior to using the applicator.

The applicator 10 is then removed from the heated cup 12 and then wiped with a fabric material 22, e.g., a coarse paper towel, to remove any cleaning composition remaining on the applicator 10 and to insure that it is dry FIG. 6. The applicator is then reused for a subsequent application of hair removal composition.

The heated cleaning composition 18 provides a warm applicator 10 that gives the technician the ability to use less hair removal product on the applicator 10, thus saving time and money for the salon.

The heater cup 12 for the cleaning composition is designed to keep the temperature of the cleaning composition between 125° F. and 135° F. and is heated by electricity from a 12 volt 2.5 amps source which is also energy efficient for the salon.

Another aspect of this invention are applicator kits for applying the non-aqueous hair removal compositions of this invention. The kits may include all of the elements described herein or only some of them. The elements of such kits are seen in the Figures. Referring to the Figures, the applicator kits include:

a. A first container 16 containing the liquid non-aqueous cleaning composition 18 of this invention;

b. A second container 24 containing the non-aqueous hair removal composition;

c. A first electrically heated cup 12 for the cleaning composition, including the basket 14 and electric plug 20;

d. A second electrically heated cup for the non-aqueous hair removal composition 24, 26;

e. At least one stainless steel applicator for applying the non-aqueous hair removal composition to the skin 10;

f. Directions consisting of, for example:
  i. Filling the first heater cup 12 with an amount of the cleaning composition 18;
  ii. Heating the cleaning composition 18 contained in the cup 12 to a temperature sufficient to solubilize the non-aqueous hair removal composition to produce a heated cleaning composition;
  iii. Initially contacting the applicator 10 with the heated cleaning composition 18 for a period of time to remove any bacteria thereon; and then
  iv. Wiping the applicator with a fabric material 22 to remove any cleaning composition remaining on the applicator 10 to produce a clean applicator;
  v. Filling the second heater cup 24 with an amount of the hair removal composition 26;
  vi. Heating the hair removal composition 26 to produce a heated hair removal composition to a temperature that adequately liquefies the hair removal composition to enable application of the composition to the skin with the applicator 10;

vii. Contacting the clean applicator 10 with the heated hair removal composition 26; and then viii. Applying the hair removal composition 26 to a person's skin EB, L with the clean applicator 10 to produce a contaminated applicator having thereon a residual amount of the hair removal composition and bacteria;

ix. Contacting the contaminated applicator with the heated cleaning composition for a period of time to remove the residual amount of hair removal composition thereon and substantially all the bacteria thereon; and then x. Wiping the applicator with a fabric material 22 to remove any cleaning composition remaining on the applicator to produce a clean applicator; and then xi. Repeating steps vii through x.

It should be understood that such kits may include all of the foregoing elements or only some of these elements to carry out only a part of the process of this invention.

EXAMPLES

The invention is further illustrated by the following non limiting examples.

Example 1

Cleaning Composition Ingredients

| | |
|---|---|
| 1. Highly refined white mineral oil (Sonneborn Blandol) | 97.7% by weight. |
| 2. Triclosan (CAS Number 3380-34-5, Chem/UPAC name description 5-Chloro-2-(2,4-dichlorophenoxy) phenol) | 0.3% by weight. |
| 3. Microbial Control Neolone ® PH 100 (Dow Chemical) (Phenoxyethanol C.A.S. Reg. No. 122-99-6) | 1.0% by weight. |
| 4. Fragrance/Preservative (Phenoxy Ethanol, 1,2Hexanediol, Decylene Glycol) SymriseSymocide ® PS) | 1.0% by weight |

Procedure:

At room temperature the triclosan is dispersed and dissolved into the fragrance for solubility. When completely mixed the Phenoexyethanol is dispersed into the mixture. Then this mixture is dispersed at room temperature into the Mineral oil while stirring. Continue stirring for 30 minutes.

The end product appears slightly opaque (milky white) until heated in the heater cup 12 to 125° F., at which time it becomes clear.

Antibacterial Activity

The following methods were used in the preparation and testing of the antibacterial activity of the Cleaning Compositions of this invention:

Determination of Rapid Germicidal (Time Kill) Activity of Antibacterial Products.

The activity of the antibacterial Cleaning Compositions of this invention were measured by the time kill method, whereby the survival of challenged organisms exposed to an antibacterial test composition is determined as a function of time. In these tests, a diluted aliquot of the Cleaning Composition is brought into contact with a known population of test bacteria for a specified time period at a specified temperature. The test Cleaning Composition is neutralized at the end of the time period, which arrests the antibacterial activity of the composition. The percent or, alternatively, log reduction from the original bacteria population is calculated. This time kill method of testing the activity of antibacterial products is known to those skilled in the art.

The compositions can be tested at any concentration from 0-100% by weight. The choice of which concentration to use is at the discretion of the investigator, and suitable concentrations are readily determined by those skilled in the art. For example, viscous samples usually are tested at 50% by weight dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about 10(8) colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

ASTM E2315, *Standard Guide for Assessment of Antimicrobial Activity Using Time-Kill Procedure*, is incorporated herein by reference. This procedure is used to assess the in vitro reduction of a microbial population of test organisms after exposure to a test material.

Example 2

Test Organism(s)

*S. aureus* ATCC 6538

Experimental Design:

Time Kill Study Using 1 Part Inoculum: 9 Parts Test Product, a Modification of ASTM Method E2315.

The following test organisms are used:

1) *S. aureus* ATCC 6538

0.09 ml of SS applicator cleaner warmed to 52° C. are mixed with 0.01 ml of a culture diluted-$10^{-1}$ (prepared from an overnight culture (approx 22 hours old) diluted to 0.45 OD at 600 nm), and mixed for 15 seconds. After the time has elapsed, 4.9 ml of DIE broth is added to the reaction tube to quench antimicrobial the activity. A secondary 1:100 dilution with D/E broth (0.02 ml:1.98 ml D/E broth) and tertiary dilution 1:5 (0.2 ml:0.8 ml D/E broth) is carried out and aliquots of 0.5 ml of the last two dilutions are plated. The TSA plates are incubated for 24-48 hours at 35° C. to 37° C. As a control, 0.09 ml of drug-free mineral oil is substituted for the test product and processed in the same manner as the test groups. A saline+D/E broth uninoculated blank is also subcultured to ensure sterility of the media and technique.

Note: if applicable, the different test samples are tested alternately to eliminate an order bias, e.g. sample X was tested followed by sample Y and then sample Z and back to sample X, etc.

Calculations:
# of CFU/control sample: CFU/plate×1000
# of CFU/test sample: CFU/plate×1000

Materials:
1. Cole-Parmer D/E Neutralizing Broth Lot No: 10162 Expiration Date: May 2013
2. Cleaning Compositions:
   A. NFSAC Cleaning Composition with 0.3% triclosan+0.2 BZK.
   B. NFSAC Cleaning Composition with 0.3% triclosan+1% Symocide PS.
   C. NFSAC Cleaning Composition with 0.3% triclosan+1% Symocide PS+1% Neolone PH100.

Results:

| Time kill study. | |
|---|---|
| v. *S. aureus* ATCC 6538 | |
| Control 1 # of CFU/plate: 35 | # of CFU/control sample: $3.5 \times 10^4$ |
| NFSAC-A Test 1 # of CFU/plate: 10 (2)* | # of CFU/test 1 sample: $1.0 \times 10^4$ |
| NFSAC-A Test 2 # of CFU/plate: 10 (2)* | # of CFU/test 2 sample: $1.0 \times 10^4$ |
| Average counts/sample: $1 \times 10^4$ | |
| Average reduction: 71.43% | |
| NFSAC-B Test 1 # of CFU/plate: 3 | # of CFU/test 1 sample: $3.0 \times 10^3$ |
| NFSAC-B Test 2 # of CFU/plate: 0 | # of CFU/test 2 sample: 0 |
| Average counts/sample: $1.5 \times 10^3$ | |
| Average reduction: 95.7% | |
| NFSAC-C Test 1 # of CFU/plate: 0 | # of CFU/test 1 sample: 0 |
| NFSAC-C Test 2 # of CFU/plate: 0 | # of CFU/test 2 sample: 0 |
| Average counts/sample: 0 | |
| Average reduction: >97.2% | |
| Blank Sample # of CFU/plate: 0 | |

*counts from $3^{rd}$ dilution

Conclusions: The combination of 0.3% triclosan+1% Neolone PH100+1% Symocide PS appears to be the most effective in rapidly reducing the bacterial challenge in 15 seconds. The plate counts from the third dilution were one fifth of the second dilution indicating that the triclosan carried over into the $2^{nd}$ dilution does not have an impact on recovery.

TABLE 1

| | | Cleaning Composition Time Kill Results | | | | | |
|---|---|---|---|---|---|---|---|
| Test | Control | NFSAC-A | | NFSAC-B | | NFSAC-C | |
| organism | cfu/sample | cfu/sample | % reduction | cfu/sample | % reduction | cfu/sample | % reduction |
| *S. aureus* ATCC 6538 | $3.5 \times 10^4$ | $1.0 \times 10^4$ | 71.4 | $1.5 \times 10^3$ | 95.7 | 0 | >97.2 |

Example 3
Test Organism(s)
*S. aureus* ATCC 6538

Experimental Design:
Time Kill Study Using 1 Part Inoculum: 9 Parts Test Product, a Modification of ASTM Method E2315.
The following test organisms are used:
1) *S. aureus* ATCC 6538
Note: inoculum is increased 10× compared to previous experiment to determine if the percentage reduction is antibacterial (≥99.9%)

0.09 ml of Cleaning Composition warmed to 52° C. are mixed with 0.01 ml of an overnight culture diluted to 0.45 OD at 600 nm), and mixed for 15 seconds. After the time has elapsed, 4.9 ml of DIE broth is added to the reaction tube to quench antimicrobial the activity. A secondary 1:100 dilution with D/E broth (0.02 ml:1.98 ml D/E broth) and 0.5 ml aliquots of the last dilution are plated. The TSA plates are incubated for 24-48 hours at 35° C. to 37° C. As a control, 0.09 ml of drug-free mineral oil is substituted for the test product and processed in the same manner as the test groups with an extra 1:10 dilution of which, a 0.5 ml aliquot is plated. A saline+D/E broth uninoculated blank is also subcultured to ensure sterility of the media and technique.

Note: if applicable, the different test samples are tested alternately to eliminate an order bias, e.g. sample X was tested followed by sample Y and then sample Z and back to sample X, etc.

Calculations:
# of CFU/control sample: CFU/plate×10,000
# of CFU/test sample: CFU/plate×1000

Materials:
3. Cole-Parmer D/E Neutralizing Broth Lot No: 10162 Expiration Date: May 2013
4. Stainless steel applicator cleaners:
   B) NFSAC Cleaning Composition with 0.3% triclosan+1% Symocide PS.
   C) NFSAC Cleaning Composition with 0.3% triclosan+1% Symocide PS+1% Neolone PH100.

Results:

| Time kill study. | |
|---|---|
| v. *S. aureus* ATCC 6538 | |
| Control 1 # of CFU/plate: 544 | # of CFU/control sample: $5.44 \times 10^6$ |
| NFSAC-B Test 1 # of CFU/plate: 315 | # of CFU/test 1 sample: $3.2 \times 10^5$ |
| NFSAC-B Test 2 # of CFU/plate: 288 | # of CFU/test 2 sample: $2.9 \times 10^5$ |
| Average counts/sample: $3.1 \times 10^5$ | |
| Average reduction: 94.3% | |
| NFSAC-C Test 1 # of CFU/plate: 0 | # of CFU/test 1 sample: 0 |
| NFSAC-C Test 2 # of CFU/plate: 0 | # of CFU/test 2 sample: 0 |
| Average counts/sample: 0 | |
| Average reduction: >99.98% | |
| Blank Sample # of CFU/plate: 0 | |

Conclusions: The combination of 0.3% triclosan+1% Neolone PH100+1% Symocide PS (NFSAC-C) is the preferred composition for antibacterial activity. The higher challenge inoculum allows for determination of whether the % reduction meets antibacterial levels, i.e. ≥99.9%.

TABLE 2

Cleaning Composition Time Kill Results

| Test organism | Control cfu/sample | NFSAC-B cfu/sample | NFSAC-B % reduction | NFSAC-C cfu/sample | NFSAC-C % reduction |
|---|---|---|---|---|---|
| S. aureus ATCC 6538 | $5.44 \times 10^6$ | $3.1 \times 10^5$ | 94.3 | 0 | >99.98 |

Example 4

Test Organism(s)

S. aureus ATCC 6538

Experimental Design:
Time Kill Study Using 1 Part Inoculum: 9 Parts Test Product, a Modification of ASTM Method E2315.
The following test organisms are used:
1) S. aureus ATCC 6538
Note: inoculum is increased 10× compared to previous experiment to determine if the percentage reduction is antibacterial (≥99.9%)

0.09 ml of SS applicator cleaner warmed to 52° C. are mixed with 0.01 ml of an overnight culture diluted to 0.45 OD at 600 nm), and mixed for 15 seconds. After the time has elapsed, 4.9 ml of D/E broth is added to the reaction tube to quench antimicrobial the activity. A secondary 1:100 dilution with D/E broth (0.02 ml:1.98 ml D/E broth) and 0.5 ml aliquots of the last dilution are plated. The TSA plates are incubated for 24-48 hours at 35° C. to 37° C. As a control, 0.09 ml of drug-free mineral oil is substituted for the test product and processed in the same manner as the test groups with an extra 1:10 dilution of which, a 0.5 ml aliquot is plated. A saline+D/E broth uninoculated blank is also subcultured to ensure sterility of the media and technique.
Note: if applicable, the different test samples are tested alternately to eliminate an order bias, e.g. sample X was tested followed by sample Y and then sample Z and back to sample X, etc.
Calculations:
# of CFU/control sample: CFU/plate×10,000
# of CFU/test sample: CFU/plate×1000
Materials:
1. Cole-Parmer D/E Neutralizing Broth Lot No: 10162 Expiration Date: May 2013
   2. Stainless steel applicator cleaners:
   A NFSAC Cleaning Composition with 0.3% triclosan+1% Symocide PS.
3. DifcoTSA
4. Cole-Parmer TSB Results:

Time kill study.

v. S. aureus ATCC 6538

Control 1 # of CFU/plate: 240      # of CFU/control sample: $2.4 \times 10^6$
NFSAC-B Test 1 # of CFU/plate: 2   # of CFU/test 1 sample: $2 \times 10^3$
NFSAC-B Test 2 # of CFU/plate: 0   # of CFU/test 2 sample: 0
Average counts/sample: $1.0 \times 10^3$
Average reduction: 99.96%
Blank Sample # of CFU/plate: 0

Conclusions: The combination of 0.3% triclosan+1% Neolone PH100+1% Symocide PS appears to meet the criteria for antibacterial claims. The higher challenge inoculum allows for determination of whether the % reduction meets antibacterial levels, i.e. ≥99.9%.

TABLE 3

Cleaning Composition Time Kill Results

| Test organism | Control cfu/sample | NFSAC Cleaning Compositions $\bar{X}$ cfu/sample | % reduction |
|---|---|---|---|
| S. aureus ATCC 6538 | $5.44 \times 10^6$ | $1.0 \times 10^3$ | 99.96 |

Example 5

Test Organism(s)

S. aureus ATCC 6538

Experimental Design:
Time Kill Study Using 1 Part Inoculum: 9 Parts Test Product, a Modification of ASTM Method E2315.
The following test organisms are used:
1) S. aureus ATCC 6538
Note: inoculum is increased 10× compared to previous experiment to determine if the percentage reduction is antibacterial (≥99.9%)

0.09 ml aliquot of Cleaning Composition warmed to 52° C. is mixed with 0.01 ml of an overnight culture diluted to 0.45 OD at 600 nm), and mixed for 15 seconds. After the time has elapsed, 4.9 ml of DIE broth is added to the reaction tube to quench antimicrobial the activity. A secondary 1:100 dilution with D/E broth (0.02 ml:1.98 ml D/E broth) and 0.5 ml aliquots of the last dilution are plated. The TSA plates are incubated for 24-48 hours at 35° C. to 37° C. As a control, 0.09 ml of drug-free mineral oil is substituted for the test product and processed in the same manner as the test groups with an extra 1:10 dilution of which, a 0.5 ml aliquot is plated. A saline+D/E broth uninoculated blank is also subcultured to ensure sterility of the media and technique.
Note: if applicable, the different test samples are tested alternately to eliminate an order bias, e.g. sample X was tested followed by sample Y and then sample Z and back to sample X, etc.
Calculations:
# of CFU/control sample: CFU/plate×10,000
# of CFU/test sample: CFU/plate×1000

Materials:
1. Cole-Parmer D/E Neutralizing Broth Lot No: 10162 Expiration Date: May 2013
2. Stainless steel applicator cleaners:
   A. NFSAC Cleaning Composition with 0.3% triclosan+1% Symocide PS.
3. DifcoTSA
4. Cole-Parmer TSB Results:

Time kill study.

v. *S. aureus* ATCC 6538

Control 1 # of CFU/plate: 240       # of CFU/control sample: $2.4 \times 10^6$
NFSAC-B Test 1 # of CFU/plate: 2    # of CFU/test 1 sample: $2 \times 10^3$
NFSAC-B Test 2 # of CFU/plate: 0    # of CFU/test 2 sample: 0
Average counts/sample: $1.0 \times 10^3$
Average reduction: 99.96%
Blank Sample # of CFU/plate: 0

Conclusions: The combination of 0.3% triclosan+1% Neolone PH100+1% Symocide PS appears to meet the criteria for antibacterial claims. The higher challenge inoculum allows for determination of whether the % reduction meets antibacterial levels, i.e. ≥99.9%.

TABLE 4

Cleaning Composition Time Kill Results

| Test organism | Control cfu/sample | NFSAC Cleaning Compositions X̄ cfu/sample | % reduction |
|---|---|---|---|
| *S. aureus* ATCC 6538 | $5.44 \times 10^6$ | $1.0 \times 10^3$ | 99.96 |

Example 6

Test Organism(s)

*E. coli* ATCC 8739

Experimental Design:
Time Kill Study Using 1 Part Inoculum: 9 Parts Test Product, a Modification of ASTM Method E2315.
The following test organisms are used:
1) *E. coli* ATCC 8739
Note: inoculum is increased 10× compared to previous experiment to determine if the percentage reduction is antibacterial (≥99.9%).
  0.09 ml aliquot of SS applicator cleaner warmed to 52° C. is mixed with 0.01 ml of an overnight culture diluted to 0.45 OD at 600 nm), and mixed for 15 seconds. After the time has elapsed, 4.9 ml of D/E broth is added to the reaction tube to quench antimicrobial the activity. A secondary 1:100 dilution with D/E broth (0.02 ml:1.98 ml D/E broth) and 0.5 ml aliquots of the last dilution are plated. The TSA plates are incubated for 24-48 hours at 35° C. to 37° C. As a control, 0.09 ml of drug-free mineral oil is substituted for the test product and processed in the same manner as the test groups with an extra 1:10 dilution of which, a 0.5 ml aliquot is plated. A saline+D/E broth uninoculated blank is also subcultured to ensure sterility of the media and technique.
Note: if applicable, the different test samples are tested alternately to eliminate an order bias, e.g. sample X was tested followed by sample Y and then sample Z and back to sample X, etc.

Calculations:
# of CFU/control sample: CFU/plate×10,000
# of CFU/test sample: CFU/plate×1000
Materials:
1. Cole-Parmer D/E Neutralizing Broth Lot No: 10162 Expiration Date: May 2013
2. Stainless steel applicator cleaners:
   a) NFSAC Cleaning Composition with 0.3% triclosan+1% Symocide PS.
3. DifcoTSA
4. Cole-Parmer TSB Results:

Time kill study.

v. *E. coli* ATCC 8739

Control 1 # of CFU/plate: 568       # of CFU/control sample: $5.7 \times 10^6$
NFSAC-B Test 1 # of CFU/plate: 4    # of CFU/test 1 sample: $4 \times 10^3$
NFSAC-B Test 2 # of CFU/plate: 0    # of CFU/test 2 sample: 0
Average counts/sample: $1.0 \times 10^3$
Average reduction: 99.97%
Blank Sample # of CFU/plate: 0

Conclusions: The combination of 0.3% triclosan+1% Neolone PH100+1% Symocide PS appears to meet the criteria for antibacterial claims at 15 seconds. The higher challenge inoculum allows for determination of whether the % reduction meets antibacterial levels, i.e. ≥99.9%.

TABLE 5

Cleaning Composition Time Kill Results

| Test organism | Control cfu/sample | NFSAC Cleaning Compositions X̄ cfu/sample | % reduction |
|---|---|---|---|
| *E. coli* ATCC 8739 | $5.7 \times 10^6$ | $4.0 \times 10^3$ | 99.97 |

Example 7

Test Organism(s)

*Candida albicans* ATCC 10231

Experimental Design:
Time Kill Study Using 1 Part Inoculum: 9 Parts Test Product, a Modification of ASTM Method E2315.
The following test organisms are used:
1) *Candida albicans* ATCC 10231
  0.09 ml aliquot of SS applicator cleaner warmed to 52° C. is mixed with 0.01 ml of an overnight culture diluted to 0.45 OD at 600 nm), and mixed for 15 seconds. After the time has elapsed, 4.9 ml of DIE broth is added to the reaction tube to quench antimicrobial the activity. A secondary 1:100 dilution with D/E broth (0.02 ml:1.98 ml D/E broth) and 0.5 ml aliquots of the last dilution are plated. The SDA plates are incubated for 24-48 hours at 35° C. to 37° C. As a control, 0.09 ml of drug-free mineral oil is substituted for the test product and processed in the same manner as the test groups with an extra 1:10 dilution of which, a 0.5 ml aliquot is plated. A saline+D/E broth uninoculated blank is also subcultured to ensure sterility of the media and technique.
Note: if applicable, the different test samples are tested alternately to eliminate an order bias, e.g. sample X was tested followed by sample Y and then sample Z and back to sample X, etc.

Calculations:
# of CFU/control sample: CFU/plate×10,000
# of CFU/test sample: CFU/plate×1000
Materials:
1. Cole-Parmer D/E Neutralizing Broth Lot No: 10162
Expiration Date: May 2013
  2. Stainless steel applicator cleaners:
    a) NFSAC Cleaning Composition with 0.3% triclosan+1% Symocide PS.
  3. BD/Difco SDA
  4. Cole-Parmer SDB
Results:

| Time kill study. | |
|---|---|
| v. *Candida albicans* ATCC 10231 | |
| Control 1 # of CFU/plate: 209 | # of CFU/control sample: $2.1 \times 10^6$ |
| NFSAC-B Test 1 # of CFU/plate: 2 | # of CFU/test 1 sample: $2 \times 10^3$ |
| NFSAC-B Test 2 # of CFU/plate: 4 | # of CFU/test 2 sample: $4 \times 10^3$ |
| Average counts/sample: $1.0 \times 10^3$ | |
| Average reduction: 99.86% | |
| Blank Sample # of CFU/plate: 0 | |

Conclusions: The combination of 0.3% triclosan+1% Neolone PH100+1% Symocide PS appears to meet the criteria for antibacterial claims when the average reduction is rounded to the nearest tenth.

TABLE 6

Cleaning Composition Time Kill Results

| Test organism | Control cfu/sample | NFSAC Cleaning Compositions $\bar{X}$ cfu/sample | % reduction |
|---|---|---|---|
| *Candida albicans* ATCC 10231 | $2.1 \times 10^6$ | $3.0 \times 10^3$ | 99.86 |

Example 8

Test Organism(s)

MRSA ATCC 33592

Experimental Design:
Time Kill Study Using 1 Part Inoculum: 9 Parts Test Product, a Modification of ASTM Method E2315.
The following test organisms are used:
1) MRSA ATCC 33592
Note: inoculum is increased 10× compared to previous experiment to determine if the percentage reduction is antibacterial (≥99.9%).

0.09 ml aliquot of SS applicator cleaner warmed to 52° C. is mixed with 0.01 ml of an overnight culture diluted to 0.45 OD at 600 nm), and mixed for 15 seconds. After the time has elapsed, 4.9 ml of DIE broth is added to the reaction tube to quench antimicrobial the activity. A secondary 1:100 dilution with D/E broth (0.02 ml:1.98 ml D/E broth) and 0.5 ml aliquots of the last dilution are plated. The TSA plates are incubated for 24-48 hours at 35° C. to 37° C. As a control, 0.09 ml of drug-free mineral oil is substituted for the test product and processed in the same manner as the test groups with an extra 1:10 dilution of which, a 0.5 ml aliquot is plated. A saline+D/E broth uninoculated blank is also subcultured to ensure sterility of the media and technique.
Note: if applicable, the different test samples are tested alternately to eliminate an order bias, e.g. sample X was tested followed by sample Y and then sample Z and back to sample X, etc.
Calculations:
# of CFU/control sample: CFU/plate×10,000
# of CFU/test sample: CFU/plate×1000
Materials:
1. Cole-Parmer D/E Neutralizing Broth Lot No: 10162
Expiration Date: May 2013
  2. Stainless steel applicator cleaners:
    a) NFSAC Cleaning Composition with 0.3% triclosan+1% Symocide PS.
  3. DifcoTSA
  4. Cole-Parmer TSB
Results:

| Time kill study. | |
|---|---|
| v. MRSA ATCC 33592 | |
| Control 1 # of CFU/plate: 392 | # of CFU/control sample: $3.9 \times 10^6$ |
| NFSAC-B Test 1 # of CFU/plate: 2 | # of CFU/test 1 sample: $2 \times 10^3$ |
| NFSAC-B Test 2 # of CFU/plate: 5 | # of CFU/test 2 sample: $5 \times 10^3$ |
| Average counts/sample: $3.5 \times 10^3$ | |
| Average reduction: 99.91% | |
| Blank Sample # of CFU/plate: 0 | |

Conclusions: The combination of 0.3% triclosan+1% Neolone PH100+1% Symocide PS appears to meet the criteria for antibacterial claims at 15 seconds. The higher challenge inoculum allows for determination of whether the % reduction meets antibacterial levels, i.e. ≥99.9%.

TABLE 7

Cleaning Composition Time Kill Results

| Test organism | Control cfu/sample | NFSAC Cleaning Compositions $\bar{X}$ cfu/sample | % reduction |
|---|---|---|---|
| MRSA ATCC 33592 | $3.9 \times 10^6$ | $3.5 \times 10^3$ | 99.91 |

The invention claimed is:
1. A liquid non-aqueous cleaning composition for a stainless steel applicator used for applying non-aqueous hair removal composition to a person's skin, comprising:
  a. About 96.5% to about 98.9% by weight of a mineral oil;
  b. About 0.1% to about 0.5% by weight of triclosan;
  c. About 0.5% to about 1.5% by weight of phenoxyethanol; and
  d. About 0.5% to about 1.5% by weight of a fragrance.
2. A method of cleaning a contaminated applicator used for applying a non-aqueous hair removal composition to a person's skin, comprising:
  a. Providing a liquid non-aqueous cleaning composition comprising a solubilizing oil effective for solubilizing the non-aqueous hair removal composition and an effective antibacterial amount of an antibacterial agent;
  b. Providing a heater cup;
  c. Filling the heater cup with an amount of the cleaning composition;

d. Heating the cleaning composition contained in the cup to a temperature sufficient to solubilize the non-aqueous hair removal composition to produce a heated cleaning composition;
e. Providing a contaminated applicator having thereon a residual amount of the hair removal composition and bacteria;
f. Contacting the stainless steel applicator with the heated cleaning composition for a period of time to remove the residual amount of hair removal composition thereon and substantially all the bacteria thereon; and then
g. Wiping the stainless steel applicator with a fabric material to remove any cleaning composition remaining on the stainless steel applicator;
h. Applying to the person's skin with the stainless steel applicator the hair removal composition to produce the contaminated applicator;
i. Repeating steps f through i.

3. A method of cleaning a contaminated applicator used for applying a non-aqueous hair removal composition to a person's skin, comprising:
a. Providing a liquid non-aqueous cleaning composition comprising a mineral oil and an effective antibacterial amount of an antibacterial agent;
b. Providing a heater cup;
c. Filling the heater cup with an amount of the cleaning composition;
d. Heating the cleaning composition contained in the cup at a temperature between about 115° F. to about 135° F. to produce a heated cleaning composition;
e. Providing a contaminated applicator having thereon a residual amount of the hair removal composition and bacteria;
f. Contacting the applicator with the heated cleaning composition for a period of time to remove the residual amount of hair removal composition thereon and substantially all the bacteria thereon; and then
g. Wiping the applicator with a fabric material to remove any cleaning composition remaining on the applicator;
h. Applying to a person's skin with the applicator the hair removal composition to produce the contaminated applicator;
i. Repeating steps f through i.

4. The method of claim 3, wherein the antibacterial agent is triclosan.

5. The method of claim 3, wherein the liquid non-aqueous cleaning composition comprises:
a. About 96.5% to about 98.9% by weight of a mineral oil;
b. About 0.1% to about 0.5% by weight of triclosan;
c. About 0.5% to about 1.5% by weight phenoxyethanol; and
d. About 0.5% to about 1.5% by weight of a fragrance.

6. The method of claim 3, wherein the applicator is surgical stainless steel.

7. A method of removing hair from a person's skin, comprising:
a. Providing a heated non-aqueous hair removal composition;
b. Providing a liquid non-aqueous cleaning composition comprising a solubilizing oil effective for solubilizing the non-aqueous hair removal composition and an effective antibacterial amount of an antibacterial agent;
c. Providing a heater cup;
d. Filling the heater cup with an amount of the cleaning composition;
e. Heating the cleaning composition contained in the cup to a temperature sufficient to solubilize the non-aqueous hair removal composition to produce a heated cleaning composition;
f. Providing an applicator for applying the hair removal composition to a person's skin;
g. Contacting the applicator with the hair removal composition to provide an applicator having the hair removal composition thereon; and then
h. Applying the hair removal composition to a person's skin with the applicator to produce a contaminated applicator having thereon a residual amount of the hair removal composition and bacteria;
i. Removing the hair removal composition from the person's skin to remove the hair from the person's skin;
j. Contacting the contaminated applicator with the heated cleaning composition for a period of time to remove the residual amount of hair removal composition thereon and substantially all the bacteria thereon; and then
k. Wiping the applicator with a fabric material to remove any cleaning composition remaining on the applicator;
l. Repeating steps g through k.

8. A method of removing hair from a person's skin, comprising:
a. Providing a heated non-aqueous hair removal composition;
b. Providing a liquid non-aqueous cleaning composition comprising a mineral oil and an effective antibacterial amount of an antibacterial agent;
c. Providing a heater cup;
d. Filling the heater cup with an amount of the cleaning composition;
e. Heating the cleaning composition contained in the cup at a temperature between about 115° F. to about 135° F. to produce a heated cleaning composition;
f. Providing an applicator for applying the hair removal composition to the person's skin;
g. Contacting the applicator with the hair removal composition to provide an applicator having the hair removal composition thereon; and then
h. Applying the hair removal composition to the person's skin with the applicator to produce the contaminated applicator having thereon a residual amount of the hair removal composition and bacteria;
i. Removing the hair removal composition from the person's skin to remove the hair from the skin;
j. Contacting the contaminated applicator with the heated cleaning composition for a period of time to remove the residual amount of hair removal composition thereon and substantially all the bacteria thereon; and then
k. Wiping the applicator with a fabric material to remove any cleaning composition remaining on the applicator;
l. Repeating steps g through k.

9. The method of claim 8, wherein the antibacterial agent is triclosan.

10. The method of claim 8, wherein the liquid non-aqueous cleaning composition comprises:
a. About 96.5% to about 98.9% by weight of a mineral oil;
b. About 0.1% to about 0.5% by weight of triclosan;
c. About 0.5% to about 1.5% by weight of phenoxyethanol; and
d. About 0.5% to about 1.5% by weight of a fragrance.

11. The method of claim 8, wherein the applicator is surgical stainless steel.

12. An applicator kit for applying a non-aqueous hair removal composition to a person's skin comprising:

a. A first container containing a liquid non-aqueous cleaning composition comprising a solubilizing oil effective for solubilizing the non-aqueous hair removal composition and an effective antibacterial amount of an antibacterial agent;
b. A first electrically heated cup for the cleaning composition;
c. At least one stainless steel applicator for applying the non-aqueous hair removal composition to the skin;
d. Directions consisting of:
   i. Filling the first heater cup with an amount of the cleaning composition;
   ii. Heating the cleaning composition contained in the cup to a temperature sufficient to solubilize the non-aqueous hair removal composition to produce a heated cleaning composition;
   iii. Initially contacting the applicator with the heated cleaning composition for a period of time to remove any bacteria thereon; and then
   iv. Wiping the applicator with a fabric material to remove any cleaning composition remaining on the applicator to produce a clean applicator; and then
   v. Applying the hair removal composition to the person's skin with the clean applicator to produce a contaminated applicator having thereon a residual amount of the hair removal composition and bacteria;
   vi. Contacting the contaminated applicator with the heated cleaning composition for a period of time to remove the residual amount of hair removal composition thereon and substantially all the bacteria thereon; and then
   vii. Wiping the applicator with a fabric material to remove any cleaning composition remaining on the applicator to produce a clean applicator; and then
   viii. Repeating steps v. through vii.

13. The applicator kit of claim 12, wherein the liquid non-aqueous cleaning composition comprises:
   a. About 96.5% to about 98.9% by weight of the solubilizing oil, wherein the solubilizing oil is mineral oil;
   b. About 0.1% to about 0.5% by weight of the antibacterial agent, wherein the antibacterial agent is triclosan;
   c. About 0.5% to about 1.5% by weight of phenoxyethanol; and
   d. About 0.5% to about 1.5% by weight of a fragrance;
   e. Wherein the heating step ii. in the directions provides for heating the cleaning composition contained in the cup at a temperature between about 115° F. to about 135° F. to produce a heated cleaning composition.

14. An applicator kit for applying a non-aqueous hair removal composition to a person's skin comprising:
   a. A first container containing a liquid non-aqueous cleaning composition comprising a solubilizing oil effective for solubilizing the non-aqueous hair removal composition and an effective antibacterial amount of an antibacterial agent;
   b. A second container containing the non-aqueous hair removal composition;
   c. A first electrically heated cup for the cleaning composition;
   d. A second electrically heated cup for the non-aqueous hair removal composition;
   e. At least one stainless steel applicator for applying the non-aqueous hair removal composition to the skin;
   f. Directions consisting of:
      i. Filling the first heater cup with an amount of the cleaning composition;
      ii. Heating the cleaning composition contained in the cup to a temperature sufficient to solubilize the non-aqueous hair removal composition to produce a heated cleaning composition;
      iii. Initially contacting the applicator with the heated cleaning composition for a period of time to remove any bacteria thereon; and then
      iv. Wiping the applicator with a fabric material to remove any cleaning composition remaining on the applicator to produce a clean applicator;
      v. Filling the second heater cup with an amount of the hair removal composition;
      vi. Heating the hair removal composition to produce a heated hair removal composition to a temperature that adequately liquefies the hair removal composition to enable application of the composition to the skin with the applicator;
      vii. Contacting the clean applicator with the heated hair removal composition; and then
      viii. Applying the hair removal composition to a person's skin with the clean applicator to produce a contaminated applicator having thereon a residual amount of the hair removal composition and bacteria;
      ix. Contacting the contaminated applicator with the heated cleaning composition for a period of time to remove the residual amount of hair removal composition thereon and substantially all the bacteria thereon; and then
      x. Wiping the applicator with a fabric material to remove any cleaning composition remaining on the applicator to produce a clean applicator; and then
      xi. Repeating steps vii through x.

15. The applicator kit of claim 14, wherein the liquid non-aqueous cleaning composition comprises:
   a. About 96.5% to about 98.9% by weight of the solubilizing oil, wherein the solubilizing oil is mineral oil;
   b. About 0.1% to about 0.5% by weight of the antibacterial agent, wherein the antibacterial agent is triclosan;
   c. About 0.5% to about 1.5% by weight of phenoxyethanol; and
   d. About 0.5% to about 1.5% by weight of a fragrance.
   e. Wherein the heating step ii. in the directions provides for heating the cleaning composition contained in the cup at a temperature between about 115° F. to about 135° F. to produce a heated cleaning composition.

* * * * *